United States Patent
Butts et al.

(10) Patent No.: US 11,334,710 B2
(45) Date of Patent: May 17, 2022

(54) FRAMEWORK FOR GENERATING A TIMELINE TO MAINTAIN CONTEXT ACROSS VARIOUS DISPLAY DEVICE SIZES

(71) Applicant: CERNER INNOVATION, INC., Kansas City, KS (US)

(72) Inventors: Jody Butts, London (GB); Hannah Fiechtner, Kansas City, MO (US); Gerard Isdell, London (GB); Todd Lomaskin, Kansas City, KS (US); Christopher Luff, Middlesex (GB); Yen Mac, London (GB); Erin Musko, Kansas City, MO (US); Dhaval Patel, Crawley (GB)

(73) Assignee: CERNER INNOVATION, INC., North Kansas City, MO (US)

( * ) Notice: Subject to any disclaimer, the term of this patent is extended or adjusted under 35 U.S.C. 154(b) by 0 days.

(21) Appl. No.: 16/731,734

(22) Filed: Dec. 31, 2019

(65) Prior Publication Data

US 2021/0200941 A1 Jul. 1, 2021

(51) Int. Cl.
| | |
|---|---|
| *G06F 3/0481* | (2022.01) |
| *G06F 40/18* | (2020.01) |
| *G06F 3/0484* | (2022.01) |
| *G16H 10/60* | (2018.01) |

(52) U.S. Cl.
CPC ............ *G06F 40/18* (2020.01); *G06F 3/0481* (2013.01); *G06F 3/0484* (2013.01); *G16H 10/60* (2018.01)

(58) Field of Classification Search
None
See application file for complete search history.

(56) References Cited

U.S. PATENT DOCUMENTS

| | | | |
|---|---|---|---|
| 2005/0149361 A1 | 7/2005 | Saus et al. | |
| 2007/0073559 A1 | 3/2007 | Stangel | |
| 2009/0254370 A1* | 10/2009 | Kondo | G16H 15/00 705/3 |
| 2010/0131293 A1 | 5/2010 | Linthicum et al. | |

(Continued)

OTHER PUBLICATIONS

Non-Final Office Action received for U.S. Appl. No. 16/455,129, dated Sep. 3, 2021, 20 pages.

(Continued)

*Primary Examiner* — Rinna Yi

(74) *Attorney, Agent, or Firm* — Shook, Hardy & Bacon LLP

(57) ABSTRACT

Methods for maintaining context of data when displaying information in the form of a timeline across various display devices can be performed using a timeline generation system. The timeline generation system generates a container within a graphical user interface, where the container is proportional to a display device. A timeline is determined and segmented into columns based on the size of the container and a length of time represented by the timeline or the displayed portion of the timeline. Ranges of time represented by the columns of the timeline are provided in an intuitive manner, so that the timeline can provide easy-to-understand data regardless of timeline size or the length of time it represents. The resulting columnized timeline can be arranged on the display device based on sections of the timeline determined based on the number of columns and the size of the container.

17 Claims, 15 Drawing Sheets

(56) References Cited

U.S. PATENT DOCUMENTS

| | | |
|---|---|---|
| 2011/0184753 A1 | 7/2011 | Tripoli |
| 2012/0131507 A1 | 5/2012 | Sparandara et al. |
| 2012/0304121 A1* | 11/2012 | Cahill ................... G06F 3/0481 715/815 |
| 2013/0024206 A1 | 1/2013 | Hughes et al. |
| 2014/0068489 A1 | 3/2014 | Wyland et al. |
| 2016/0077689 A1 | 3/2016 | Audet |
| 2017/0068780 A1 | 3/2017 | Dobrean |
| 2018/0095938 A1* | 4/2018 | Monte ................... G06F 3/0488 |
| 2019/0034591 A1 | 1/2019 | Mossin et al. |
| 2020/0005911 A1 | 1/2020 | Brooks et al. |
| 2020/0005916 A1 | 1/2020 | Brooks et al. |

OTHER PUBLICATIONS

Pre-Interview First Office action received for U.S. Appl. No. 16/455,127, dated Sep. 8, 2021, 4 pages.

Final Office Action received for U.S. Appl. No. 16/455,129, dated Mar. 24, 2022, 23 pages.

\* cited by examiner

|  | 12 columns | | | | | | | | | | | |
|---|---|---|---|---|---|---|---|---|---|---|---|---|
| 1 hour | 5 m | 5 m | 5 m | 5 m | 5 m | 5 m | 5 m | 5 m | 5 m | 5 m | 5 m | 5 m |
| 2 hours | 10 m | 10 m | 10 m | 10 m | 10 m | 10 m | 10 m | 10 m | 10 m | 10 m | 10 m | 10 m |
| 4 hours | 20 m | 20 m | 20 m | 20 m | 20 m | 20 m | 20 m | 20 m | 20 m | 20 m | 20 m | 20 m |
| 8 hours | | | | | | | | | | | | |
| 12 hours | 1 hr | 1 hr | 1 hr | 1 hr | 1 hr | 1 hr | 1 hr | 1 hr | 1 hr | 1 hr | 1 hr | 1 hr |
| 24 hours | 2 hrs | 2 hrs | 2 hrs | 2 hrs | 2 hrs | 2 hrs | 2 hrs | 2 hrs | 2 hrs | 2 hrs | 2 hrs | 2 hrs |
| 48 hours | 4 hrs | 4 hrs | 4 hrs | 4 hrs | 4 hrs | 4 hrs | 4 hrs | 4 hrs | 4 hrs | 4 hrs | 4 hrs | 4 hrs |
| 8 days | | | | | | | | | | | | |
| 16 days | | | | | | | | | | | | |
| 30 days | | | | | | | | | | | | |
| 60 days | 5 d | 5 d | 5 d | 5 d | 5 d | 5 d | 5 d | 5 d | 5 d | 5 d | 5 d | 5 d |
| 90 days | | | | | | | | | | | | |
| 180 days | 15 d | 15 d | 15 d | 15 d | 15 d | 15 d | 15 d | 15 d | 15 d | 15 d | 15 d | 15 d |
| 12 months | 1 mo | 1 mo | 1 mo | 1 mo | 1 mo | 1 mo | 1 mo | 1 mo | 1 mo | 1 mo | 1 mo | 1 mo |
| 18 months | 6 wks | 6 wks | 6 wks | 6 wks | 6 wks | 6 wks | 6 wks | 6 wks | 6 wks | 6 wks | 6 wks | 6 wks |
| 4 years | 4 mos | 4 mos | 4 mos | 4 mos | 4 mos | 4 mos | 4 mos | 4 mos | 4 mos | 4 mos | 4 mos | 4 mos |

• • • CONT. FROM 3D

*FIG. 3E.*

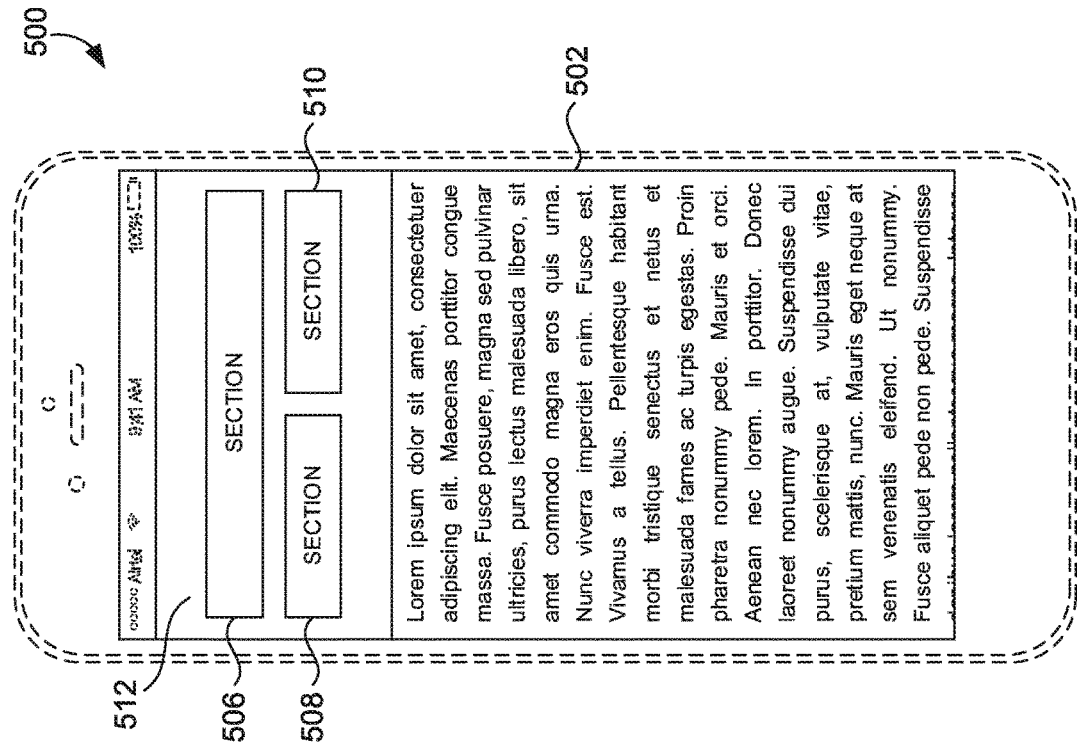
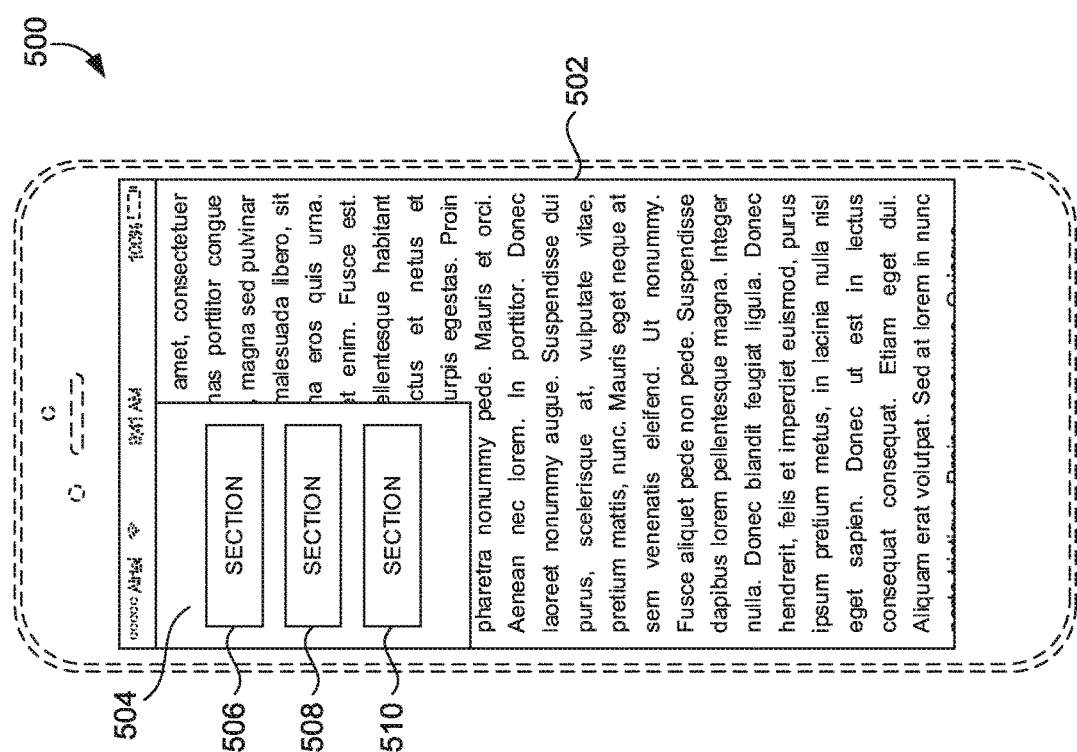
FIG. 5A.
FIG. 5B.

FRAMEWORK FOR GENERATING A TIMELINE TO MAINTAIN CONTEXT ACROSS VARIOUS DISPLAY DEVICE SIZES

BACKGROUND

Timelines are utilized across many different fields to maintain context for data. In general, timelines provide a universal way to represent information in an intuitive manner. The healthcare field utilizes patient timelines in conjunction with electronic health records to quickly understand patient information, including a patient history.

SUMMARY

At a high level, aspects described herein relate to a timeline generation system that generates timelines to maintain context across various display device sizes. This is particularly beneficial when trying to maintain context of information when the sizes of display devices vary, such as a computer desktop versus a mobile phone. Further, the technology allows context to be maintained when a user changes how information is displayed, such as rotating a mobile device to change from a landscape orientation to a portrait orientation.

One method of generating a timeline to maintain context determines a container for a display device, where the container is proportional to the display device. The container is the area in which the timeline will be displayed. A timeline for display is determined by receiving chronological information. The timeline represents a length of time over which the chronological information is included.

To determine how the timeline is displayed, a column number for the timeline is determined. The columns represent a range of time on the timeline, and each range of time comprises a fractional portion of the length of time representation. Thus, for example, if the length of time represented by the timeline is 24 hours, then the timeline could be divided into three columns that each represent a fractional portion of 8 hours. The number of columns for the timeline can be determined based on the container size and the length of time representation.

Upon determining the column number, a columnized timeline can be generated. The columnized timeline is generated by segmenting the timeline into columns based on the number. Thus, continuing with the example, if the container size supports three columns and three columns would provide an intuitive division of the length of time representation, the timeline can be segmented into three columns. The columnized timeline can be provided for display at the display device.

As noted, the timeline generation system can maintain context of the information across various display device sizes. As such, when the display device size is updated, the column number can be updated in response, as the column number is updated based on the container size, which is proportional to the display. An updated columnized timeline can then be provided to the display device. The change of display device size may occur where a user logs onto an application from a different device, or when the user changes the display device size by changing the orientation of the display.

This Summary is intended to introduce a selection of concepts in a simplified form that is further described in the Detailed Description section of this disclosure. The Summary is not intended to identify key or essential features of the claimed subject matter, nor is it intended to be used as an aid in determining the scope of the claimed subject matter. Additional objects, advantages, and novel features of the technology will be set forth in part in the description that follows, and in part will become apparent to those skilled in the art upon examination of the disclosure or learned through practice of the technology.

BRIEF DESCRIPTION OF THE DRAWINGS

The present technology is described in detail below with reference to the attached drawing figures, wherein:

Figure 3A:
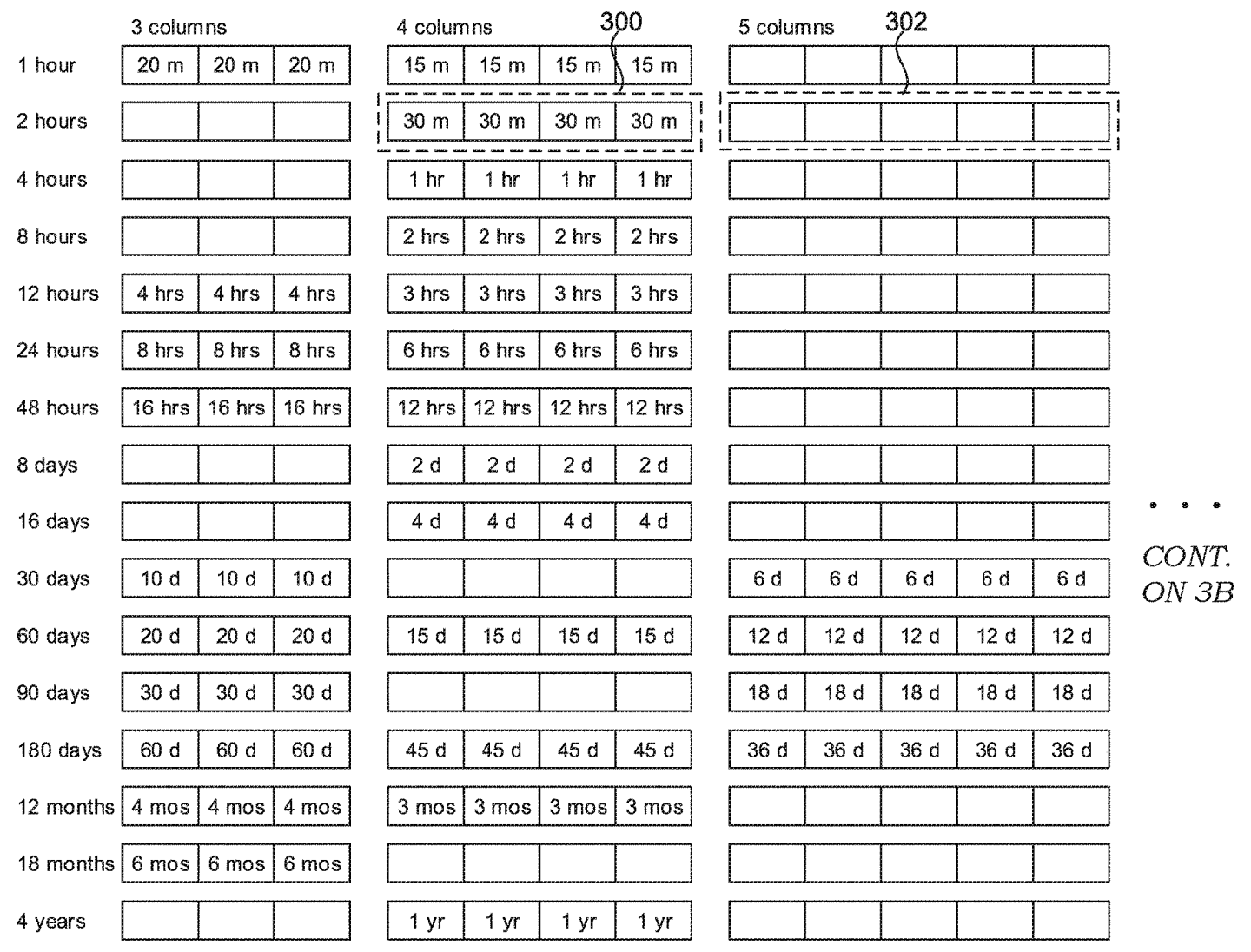
Figure 3B:
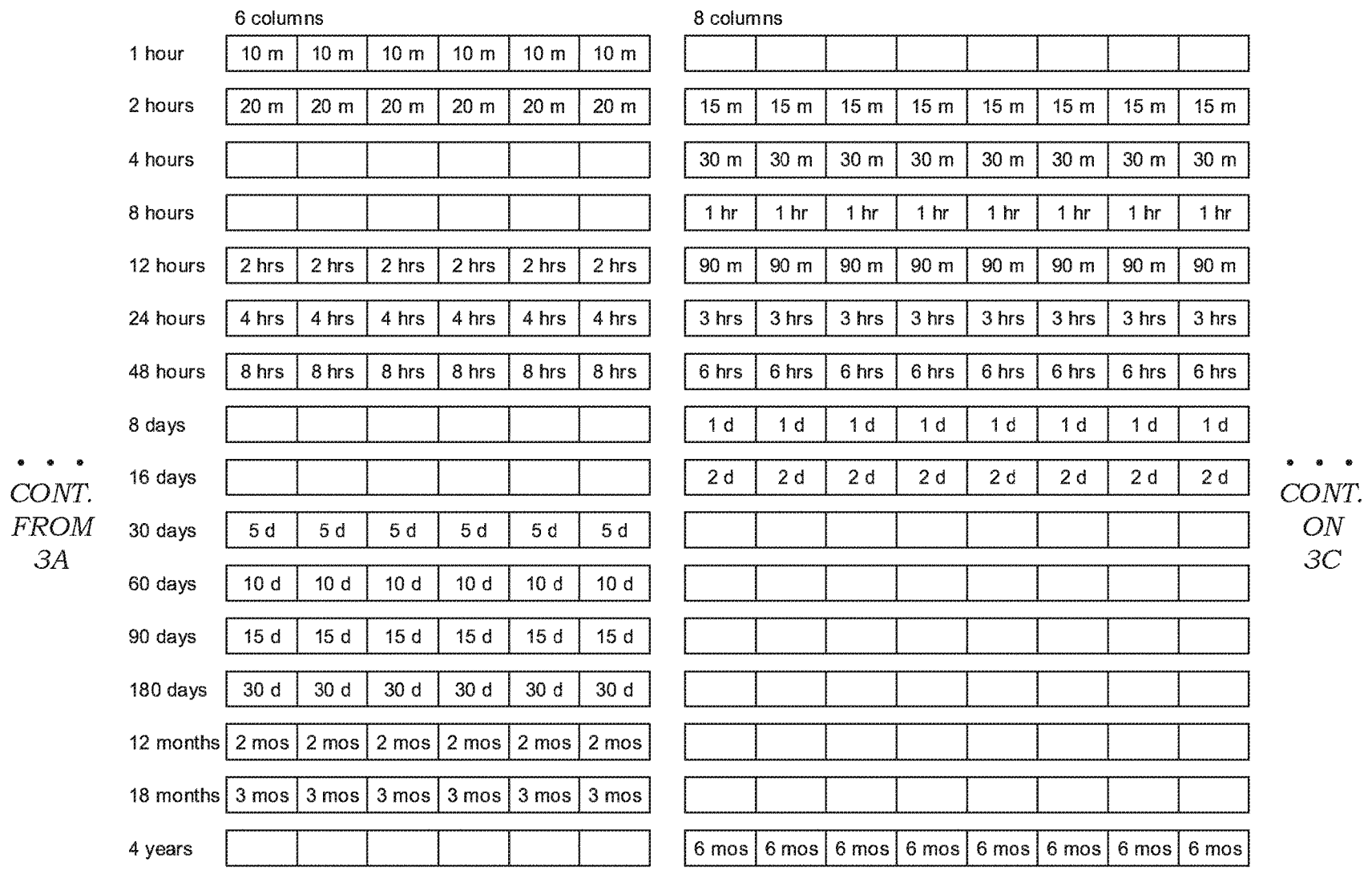
Figure 3C:
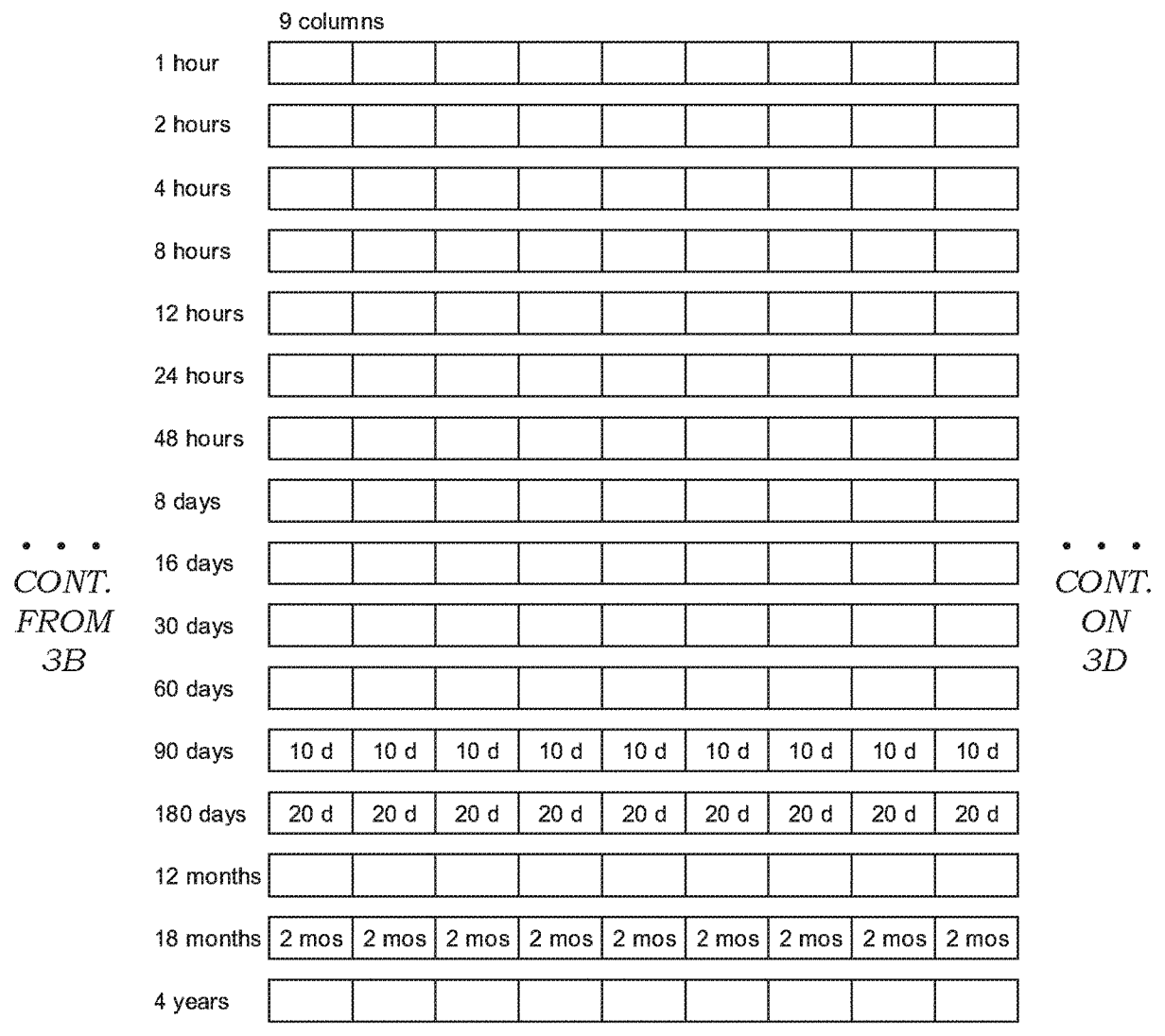
Figure 3D:
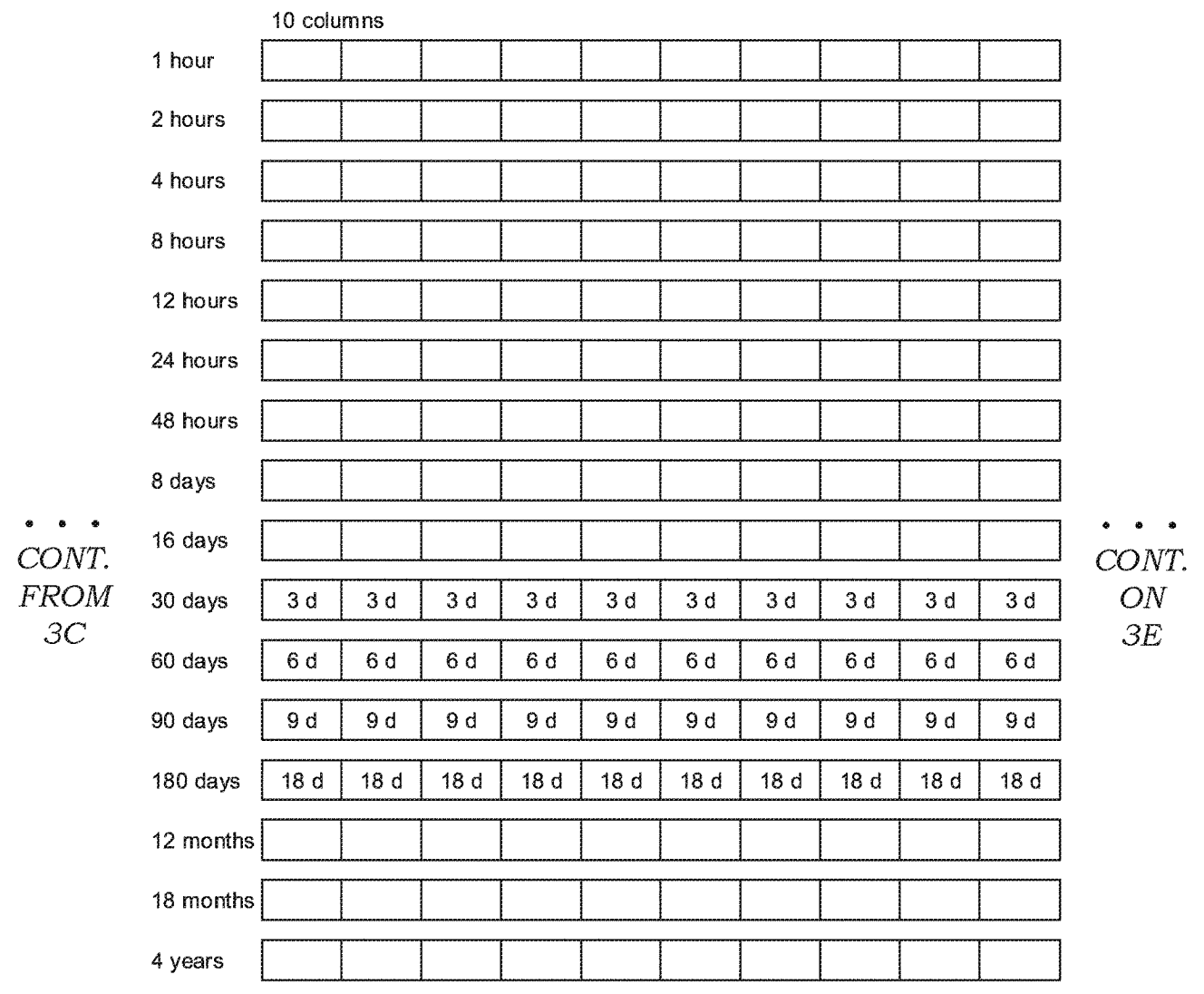

FIGS. 3A-3E illustrate an example framework for utilization by the timeline generation system of FIG. 1, in accordance with an aspect described herein;

FIG. 5A-5C illustrate a client device having a display device provided having various container sizes, in accordance with an aspect described herein;

DETAILED DESCRIPTION

Figure 1:
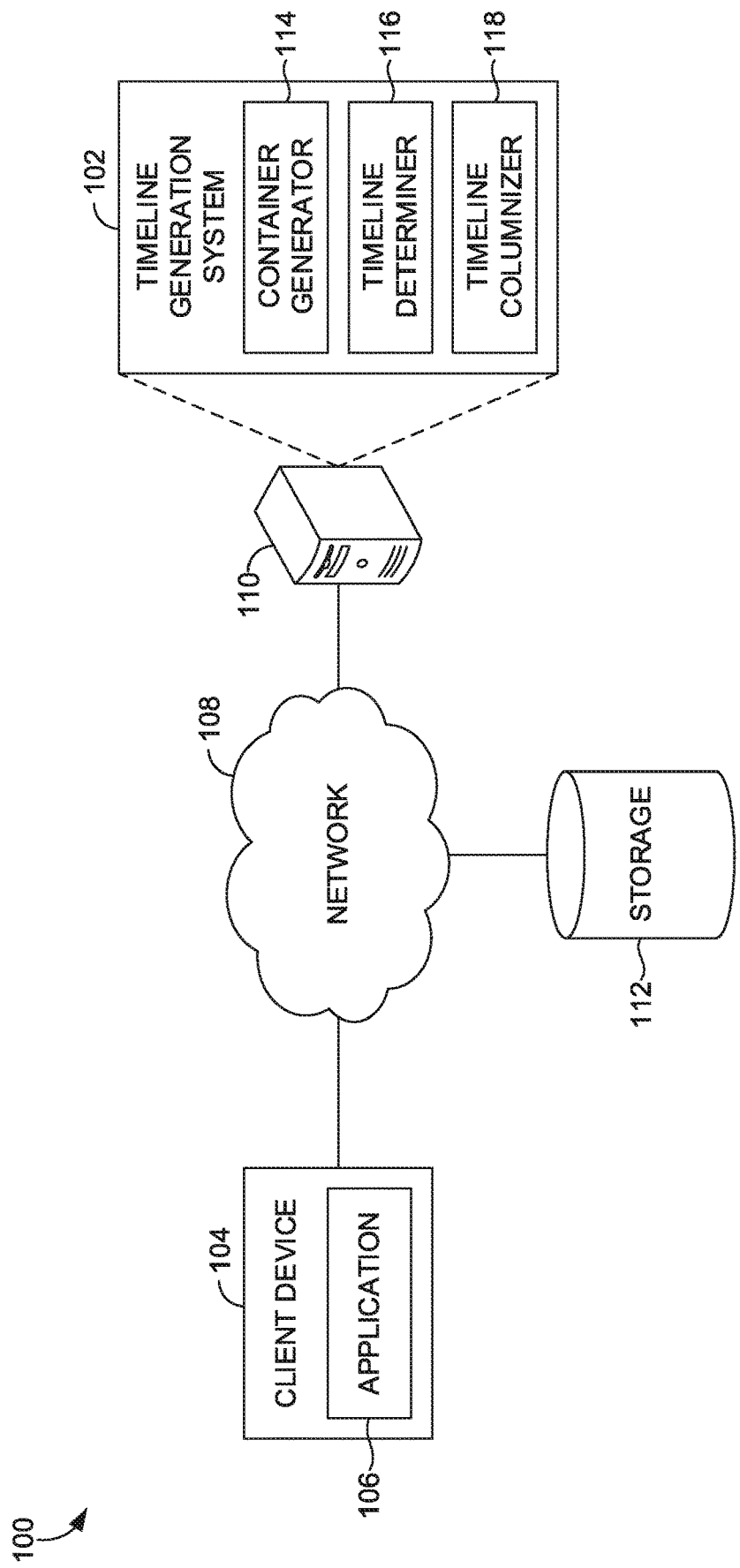
FIG. 1 is an example operating environment in which an example timeline generation system is employed, in accordance with an aspect described herein.

While timelines have been utilized to convey information, many conventional systems that provide timelines cannot maintain context across all screen sizes. That is, when information is displayed in a timeline format, it is typically displayed in the manner in which it is generated.

This presents a problem when displaying timelines across different display device sizes. For instance, if the timeline was generated for display on a desktop system having a monitor, the same timeline will be compressed when a smaller display device, such as a mobile device, is used. The timeline compression is problematic for maintaining context because the smaller area causes the information it represents to also be compressed, making it difficult or impossible to understand.

In many fields, including the field of electronic health records (EHRs), timelines are particularly helpful in conveying information, such as a patient history. However, the technology in these fields has progressed so that applications and systems interface across many different environments. In the healthcare field, a physician may log on to an EHR system using a desktop at his/her office. He or she may later use a mobile application to log on to the same system. Using conventional systems, EHR information displayed using a timeline would be compressed when changing from the desktop display device to the relatively smaller mobile display device.

The technology described herein provides for systems that address these challenges by generating timelines that maintain context across various display device sizes. That is, when screen sizes change, timelines can be regenerated to maintain context, while still providing an intuitive presentation of information.

In an example method for accomplishing these benefits, a container for a display is determined. As used herein, the term "container" refers generally to an area in which the timeline will be displayed on a display device. The "container size" is, therefore, used herein to refer to a measurement indicating the amount of space of the display device that the container uses. As noted, the timeline will be displayed within the container, and it may take up all of or a portion of the space within the container. Put another way, the timeline that is displayed within the container may extended end-to-end within the container, or may extend throughout only a portion of the container in any direction.

The container, and thus the container size, is determined proportionally to the display device. Thus, a graphical user interface that is generated with a container will have a container that is proportional to the display device by some ratio. In this way, a graphical user interface generated for a large desktop monitor will have a larger container than a relatively smaller mobile display device, which will have a smaller container based on the container being proportional to the mobile display device. As a result, the container size will be greater for the desktop monitor than it will be for the mobile device.

A timeline can be determined for display within the container. Initially, determining the timeline may include receiving information that has some chronological order. Here, the timeline comprises, or is formed from, the chronological order of the information. Thus, the timeline represents a length of time over which the chronological information is included. In some cases, the timeline represents a portion of the chronological information, and only a portion of the timeline is generated for display. In either case, the length of time over which the chronological information spans or the length of time over which a portion of the chronological information spans is termed the "length of time representation."

To generate the timeline that is displayed within the container, a column number for the timeline is determined. The columns of the timeline represent a range of time on the timeline. For instance, a single column would represent the entire length of time representation for the timeline. Two columns might represent each one-half of the length of time representation, while three might represent one-third, and so forth. Thus, each range of time for each column comprises a fractional portion of the length of time representation.

The column number can be determined based on the container size and the length of time representation. Here, the greater the container size, the more columns that can be provided as part of the timeline. That is because dividing a timeline into a large number of columns within a small area makes the information difficult to comprehend. Further, the length of time representation can affect the column number. Since the column number and the length of time representation factor into the range of time represented by each column, the column number is determined based on the length of time representation, such that the column number provides an intuitive range of time. Some examples of specific frameworks that can be used to determine the column number based on these factors will be provided.

Having determined the column number, the timeline can be segmented into columns based on the number. This generates a columnized timeline. Continuing with the same example, the column number is determined to be three and the timeline has a representation of 24 hours, then the columnized timeline is segmented into three columns, each representing an 8-hour time range, where the first column might represent 00:00-8:00; the second, 8:00-16:00; and the third, 16:00-24:00.

The columnized timeline can then be provided to a display device for display within the container. This example method may be used with various display device sizes, resulting in various timeline displays that maintain information context and provide an intuitive time display. This method can be performed automatically in response to a change in container size. Therefore, where a user views the timeline on a mobile device and changes the mobile display device orientation, such as from landscape to portrait and vice versa, the timeline is regenerated to maintain information context and provide the information in an intuitive manner based on the updated container size resulting from the orientation change.

Additionally, some aspects of timeline generation apply breakpoints to columns. The breakpoints divide the columnized timeline into sections that can be arranged in various manners when displayed. For instance, a section may include one or more columns, however, in most cases, the breakpoints are applied corresponding to section ends, so that a section does not contain a portion of a column, while another section contains the other portion. Based on the breakpoints, sections can be presented horizontal and adjacent to one another or presented vertical and adjacent to one another, which can depend on the container size.

Having described an example aspect, further description is provided with reference to the drawings. Turning first to FIG. 1, the figure depicts a block diagram of example operating environment 100 suitable for use in implementing the described technology. As illustrated, environment 100 is suitable for implementing timeline generation system 102.

It should be understood that operating environment 100 shown in FIG. 1 is an example of one suitable operating environment. Among other components not shown, operating environment 100 includes client device 104 having application 106. Client device 104 is illustrated communicating via network 108 to server 110 and storage 112. Server 110 is shown implementing timeline generation system 102.

Client devices, generally, such as client device 104, can be any type of computing device capable of being operated by a user, which may be any person or entity that provides or utilizes aspects of timeline generation system 102.

Figure 10:
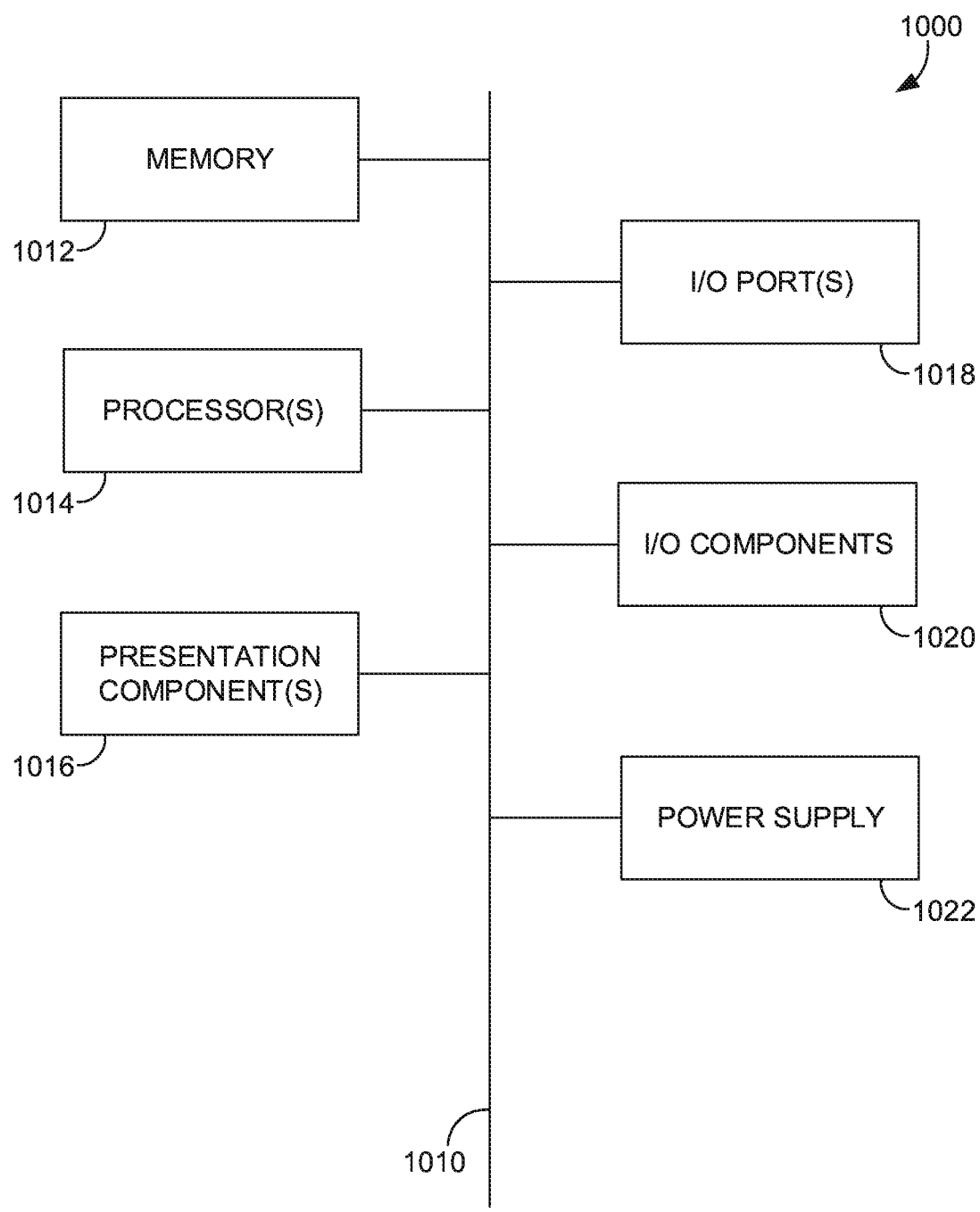
FIG. 10 is a block diagram of an example operating environment in which embodiments of the present technology may be employed.

In some implementations, client device 104 is the type of computing device described in relation to FIG. 10. For example, client device 104 may be embodied as a personal computer (PC), a laptop computer, a mobile device, a smartphone, a tablet computer, a smart watch, a wearable computer, a personal digital assistant (PDA), a global positioning system (GPS) or device, a video player, a handheld communications device, a gaming device or system, an entertainment system, a vehicle computer system, an embedded system controller, a remote control, an appliance, a consumer electronic device, a workstation, any combination of these delineated devices, or any other suitable device. Client device 104 can include a display device for displaying a graphical user interface. A suitable example is provided by I/O port 1018 of FIG. 10.

Client device 104 can include one or more processors and one or more computer-readable media. The computer-readable media may include computer-readable instructions executable by the one or more processors. The instructions may be embodied by one or more applications, such as application 106, shown in FIG. 1. Application 106 is referred to as a single application for simplicity, but its functionality can be embodied by one or more applications in practice.

Application 106 is generally capable of facilitating the exchange of information between components of FIG. 1. For example, application 106 can facilitate receiving information from a user and receiving or executing instructions provided by timeline generation system 102.

In some implementations, application 106 comprises a web application, which can run in a web browser, and could be hosted at least partially on the server-side of operating environment 100. Application 106 can comprise a dedicated application, such as an application having analytics functionality. In some cases, application 106 is integrated into the operating system (e.g., as a service or program). It is contemplated that "application" be interpreted broadly. In some embodiments, application 106 is integrated with timeline generation system 102, which is illustrated as being executed by server 110.

Server 110 generally supports timeline generation system 102. Server 110 includes one or more processors, and may comprise one or more computer-readable media. The computer-readable media includes computer-readable instructions executable by the one or more processors. The instructions may optionally implement one or more components of timeline generation system 102, described in additional detail below with reference to FIG. 2. Though illustrated as distributed in nature, components of FIG. 1 can also be integrated in any fashion, including an aspect where server 110 is integrated with client device 104.

Storage 112 generally stores information including data, computer instructions (e.g., software program instructions, routines, or services), or models used in embodiments of the described technologies. Although depicted as a database component, storage 112 may be embodied as one or more data stores or may be in the cloud. In an aspect, storage 112 may include electronic medical records stored as part of an EHR system.

As noted, server 110 can execute one or more functions of timeline generation system 102, which comprises container generator 114, timeline determiner 116, and timeline columnizer 118.

In general, container generator 114 generates a container for a graphical user interface. The generated container comprises an area in which a timeline will be displayed. Container generator 114 generates a container proportional to a size of a display device. For example, the container is generated as part of the graphical user interface. Thus, when the graphical user interface is presented at a display device, the presentation of the container will be proportional to the display device. Put another way, as the display device increases in size, a size of the container area will increase proportionally with the display device.

Container generator 114 may determine the size of the display device or the container size. The dimensions of the display device or the container can be measured in pixels ("px"). This unit of measurement is roughly equivalent to 1/96 of an inch or 0.26 millimeters. In an aspect, container generator 114 generates a container for a graphical user interface in response to detecting a change in size of the display device. This may occur where a user logs onto another device having a different display device, or where the user changes an orientation of a display device, such that it changes an aspect ratio of the display device. An example of this would be the user rotating a mobile device, which may have a non-square display, to a different position, such as landscape to portrait or vice versa. In such cases, container generator 114 can update a container size based on a change in display device or orientation of a display device.

With specific reference to FIG. 1 generally, it should be understood that this and other arrangements described herein are set forth only as examples. Other arrangements and elements (e.g., machines, interfaces, functions, orders, and groupings of functions, etc.) can be used in addition to or instead of those shown, and some elements may be omitted altogether for the sake of clarity. It should also be understood that any number of client devices, servers, and other components may be employed within operating environment 100, and such aspects are intended to be within the scope of the present disclosure. Each of the components in FIG. 1 may comprise a single device or multiple devices cooperating in a distributed environment or in the cloud.

Further, many of the elements described herein are functional entities that may be implemented as discrete or distributed components or in conjunction with other components, and in any suitable combination and location. Various functions described herein as being performed by one or more entities may be carried out by hardware, firmware, or software. For instance, some functions may be carried out by a processor executing instructions stored in memory, as will be further described with reference to FIG. 10.

Each of the components shown in FIG. 1, and within the figures generally, may be implemented via any type of computing device, such as one or more of computing device 1000 described in connection to FIG. 10, for example. These components may communicate with each other via a network, such as network 108, which may be wired, wireless, or both. Network 108 can include multiple networks, or a network of networks, but is shown in simple form so as not to obscure aspects of the present disclosure. By way of example, network 108 can include one or more wide area networks (WANs), one or more local area networks (LANs), one or more public networks such as the Internet, or one or more private networks. Where network 108 includes a wireless telecommunications network, components such as a base station, a communications tower, or even access points (as well as other components) may provide wireless connectivity. Networking environments are commonplace in offices, enterprise-wide computer networks, intranets, and the Internet. Accordingly, network 108 is not described in significant detail.

Figure 2:
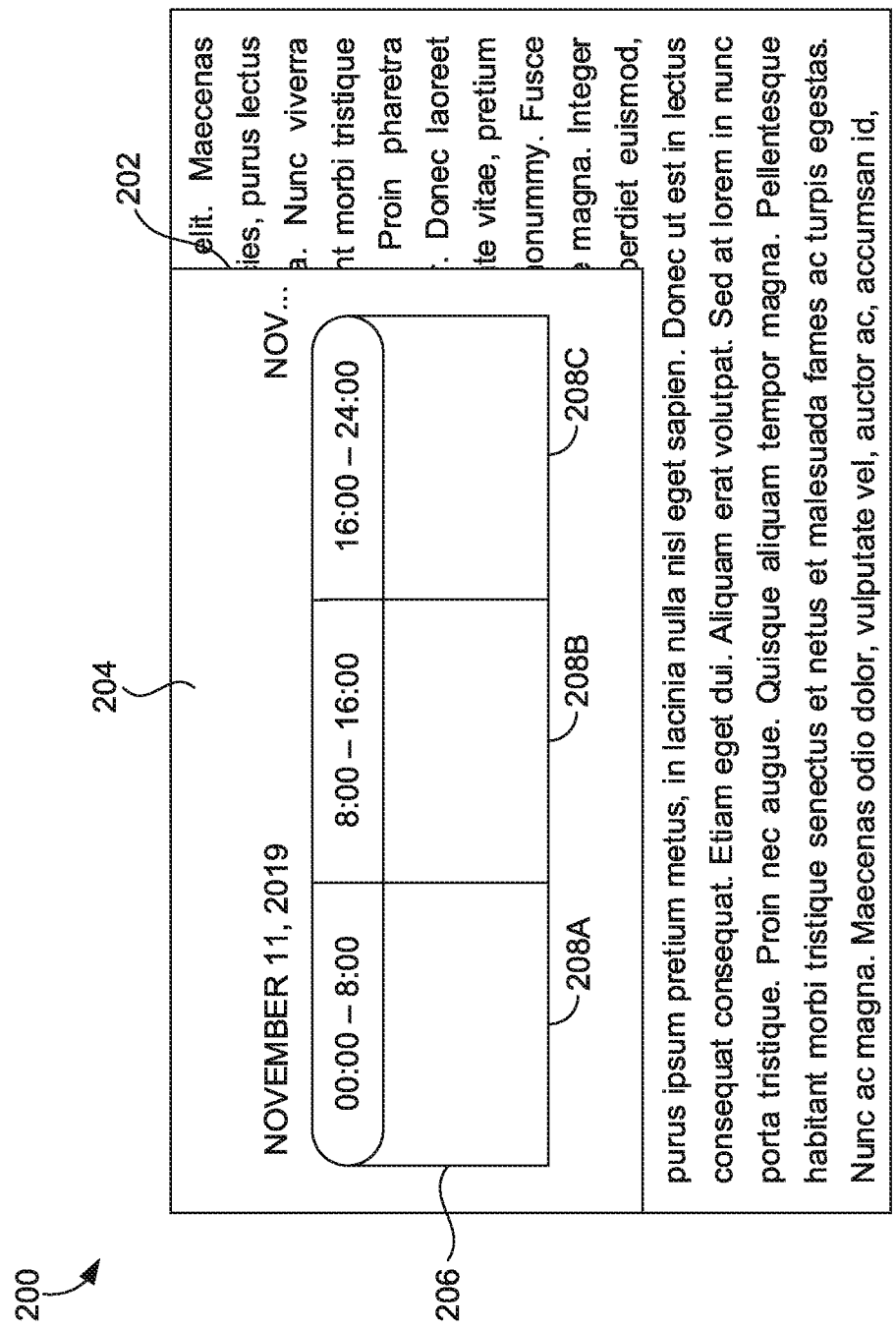
FIG. 2 is an example graphical user interface having an example timeline, in accordance with an aspect described herein.

With reference briefly to FIG. 2, an example graphical user interface 200 is provided. FIG. 2 illustrates graphical user interface 200 as comprising container 202 having a container area 204, which can be generated using container generator 114 of FIG. 1. As used herein, a container size may describe the area of a two-dimensional container or a one-dimensional element of the container, such as a length, height, width, radius, and the like. FIG. 2 further provides an example timeline 206 provided for display within container 202. It will be understood that container 202 is illustrated only to describe the technology; however, nothing is meant to impart a visual requirement for container 202. In some aspects, container 202 is not a visible part of the graphical user interface, but instead, is more theoretical in nature and defines an area of the graphical user interface. While timeline 206 is shown comprising a portion of container area 204, a generated timeline may comprise any portion of or all of a container area.

Turning back to FIG. 1, timeline generation system 102 is illustrated as further having timeline determiner 116. In general, timeline determiner 116 determines a timeline. To determine a timeline, timeline determiner 116 can receive information that has associated dates or times. Timeline determiner 116 can determine a chronological order of the received information based on the associated dates or times. In an aspect, timeline determiner 116 receives a timeline from another application, receives information having a chronological order, or receives information and determines the chronological order of the received information.

The timeline determined by timeline determiner 116 includes a length of time representation. As noted above, the length of time represented by the timeline can be all or a portion of a range of time provided by received chronological information. In an aspect, the received information includes electronic medical record information for a patient, and the determined timeline represents all or a portion of the patient's medical history. The length of time representation may include any range of time. Some examples might be 1 hour, 24 hours, 7 days, 30 days, 90 day, 1 year, 4 years, and so forth.

Timeline columnizer 118 generally segments the timeline provided by timeline determiner 116 to generate a columnized timeline. To segment the timeline, timeline columnizer 118 may determine a number of columns for the timeline. In some cases, timeline columnizer 118 segments a timeline in response to an updated container size, such as when container generator 114 updates a container size based on a change in display device or orientation of a display device.

With reference back to FIG. 2, the example timeline 206 is shown as a columnized timeline having three columns 208A-208C. Here, each column represents a range of time that is a fractional portion of the length of time representation. As shown, timeline 206 includes columns 208A-208C that together represent 24 hours, each column individually representing a range of 8 hours.

Referring back to FIG. 1, timeline columnizer 118 can determine the number of columns based on the container size and the length of time representation. As noted, to maintain the context of information, the number of columns will generally increase as the container size increases. Additionally, the column number may be based on the length of time representation, as some fractional portions of the length of time representation would not be intuitive when interpreting the data. For instance, three 8-hour columns for a 24-hour time representation may be more intuitive than five, 4.8-hour columns for the same period.

While one of ordinary skill in the art will understand from this disclosure that there are different ways to determine the column number based on these factors, a specific example framework for determining the column number is provided with reference to Table 1. Table 1 provides various column numbers as a factor of display device size and length of time representation.

TABLE 1

|   | S | M | L |
|---|---|---|---|
| 1 hour | 4 | 6 | 12 |
| 2 hours | 4 | 6 | 12 |
| 4 hours | 4 | 8 | 12 |
| 8 hours | 4 | 8 | 8 |

TABLE 1-continued

|   | S | M | L |
|---|---|---|---|
| 12 hours | 3 | 6 | 12 |
| 24 hours | 3 | 6 | 12 |
| 48 hours | 4 | 6 | 12 |
| 8 days | 4 | 8 | 8 |
| 16 days | 4 | 8 | 8 |
| 30 days | 3 | 6 | 10 |
| 60 days | 3 | 6 | 12 |
| 90 days | 3 | 6 | 9 |
| 180 days | 3 | 6 | 9 |
| 12 months | 3 | 6 | 12 |
| 18 months | 3 | 6 | 9 |
| 4 years | 4 | 8 | 12 |

In the example provided by Table 1, the table columns are labeled "S" (Small), "M" (Medium), and "L" (Large). The table columns reference small, medium, and large groups of display devices. An example categorization method comprises defining small display devices as those associated with mobile smartphone devices or smaller, including mobile smartphone devices having a display device range from 2.5 centimeters (cm)×9.5 cm to 6.5 cm×16.5 cm; medium display devices as those associated with mobile tablets, including mobile tables having a display range from 2.0 cm×13.0 cm to 14.0 cm×35.6 cm; and large display devices as those associated with computer monitors or larger, including computer monitors having a display device range from 9.0 cm×23.0 cm to 21.5 cm×78.7 cm. These are example guidelines, and other frameworks will be suitable and are contemplated within the scope of this disclosure. In another example, display devices may be considered to increase in category if the orientation changes. For example, a smartphone having a shorter width than height in one orientation may be considered a small device; however, when rotated, the width is now longer than the height in the second orientation. In the second orientation, it may be classified as a medium display device. Other predefined categories can be applied to build the framework as well.

As noted previously, the container is generated proportionally to the screen size. Thus, where the screen size is larger, the container will be larger in many cases, as well. This includes the size of the display device within a single group, such as the small devices. For instance, a container may be smaller on a display device of a small smartphone measuring 2.5 cm×9.5 cm than it will be on a small smartphone measuring 6.5 cm×16.5 cm. Since the container size increases with the size of the screen, the number of columns can be determined by timeline columnizer 118 based on the container size as it relates to the category of display device. In another embodiment, the container size may be defined based on the display device size. For instance, for small display devices, the container size can be equal to or within the range of 558 px-890 px; for medium size display devices, the container size can be equal to or within the range of 891 px-1334 px, and for a large display device, the container size can be equal to or greater than 1335 px. In another embodiment, an extra small display device may be defined. In such cases, the container size for an extra small display device might be equal to or less than 557 px. In another example, the container size of the extra small display device may be equal to or within 284 px-557 px. Thus, in one example, as the display device size increases, the container size may increase within the defined range. In another example, the display device size for a category (small, medium, large, etc.) may increase or decrease while the container size for that category remains at a fixed size, such as a size within the defined range. Both of these examples represent containers that are generated proportional to the display device.

The rows of Table 1 provide an example of some length of time representations that can be provided by a timeline. Using Table 1, the column number can be determined based on the length of time representation provided in the rows.

Combining these factors, as provided by Table 1, for a small display device having a proportional container size and a 30-day length of time representation, timeline columnizer 118 will determine the number of columns to be three, whereas for a medium display device, timeline columnizer 118 will determine the number of columns to be six. Again, this is intended to describe one aspect of the technology, and it will be understood using a different framework may result in different determinations for the number of columns.

Turning briefly to FIGS. 3A-3E, another example framework is provided. Here, another example framework is provided for determining the number of columns when generating a columnized timeline. This example framework places more emphasis on the intuitive understanding of the time range represented by each of the columns. The intuitive understanding relates to how divisions of time are provided within the timeline, so that the timeline is easily understood by a user. In general, the expansion or contraction of the timeline due to display size allows for various combinations of time divisions. Many of these divisions, however, divide the timeline into time ranges that would ultimately be confusing to a user, which disrupts the workflow and efficient utilization of the timeline. As such, some of the example frameworks described herein can be used to effectively convey the timeline using time ranges that are easy to understand, regardless of the timeline size or its length of time representation. FIGS. 3A-3E provide an example framework for providing time ranges in an intuitive manner, where the timeline size, via the container number, and the length of time representation vary.

In FIGS. 3A-3E, rows represent length of time representations of a timeline, while columns are provided in groups, such as the group labeled "3 columns," "4 columns," etc. In specific reference to FIG. 3A, intersections of some columns include data elements. For example, at intersection 300 where the row representing a 2-hour length of time representation intersects the 4-column group, data elements of "30 m" are provided. This is intended to illustrate that two hours can be intuitively segmented into four, 30-minute ranges. However, at intersection 302, where the row representing a 2-hour length of time representation intersects the 5-column group, there are no data elements. This is intended to represent that, in this particular example framework, two hours could not intuitively be segmented into five ranges of time.

Using the framework provided by FIGS. 3A-3E, the number of columns would be determined based on the length of time representation and the largest column number that could be supported by the container size. Thus, for instance, if the length of time representation by the timeline were 30 days, then timeline columnizer 118 of FIG. 1 would determine the number of columns to be three until the container size could support five columns, at which case, timeline columnizer 118 would determine the number of columns to be five. However, given that four columns for a 30-day length of time representation would result in time ranges that are not intuitive, timeline columnizer 118 may not determine a column number of four for that particular length of time representation. Again, the illustration of FIGS. 3A-3E is meant only to provide another example framework suitable for use by timeline columnizer 118. In this framework, the columns may have a predetermined pixel length in order to determine the largest column number that can be supported by a particular container size.

Having determined the number of columns, timeline columnizer 118 of FIG. 1 can segment the timeline. The timeline can be segmented based on the number of columns so that each column represents a fractional portion of the length of time representation. In some cases, each column will represent an equal fractional portion. The segmented timeline can be called a columnized timeline.

Figures 4A, 4B:
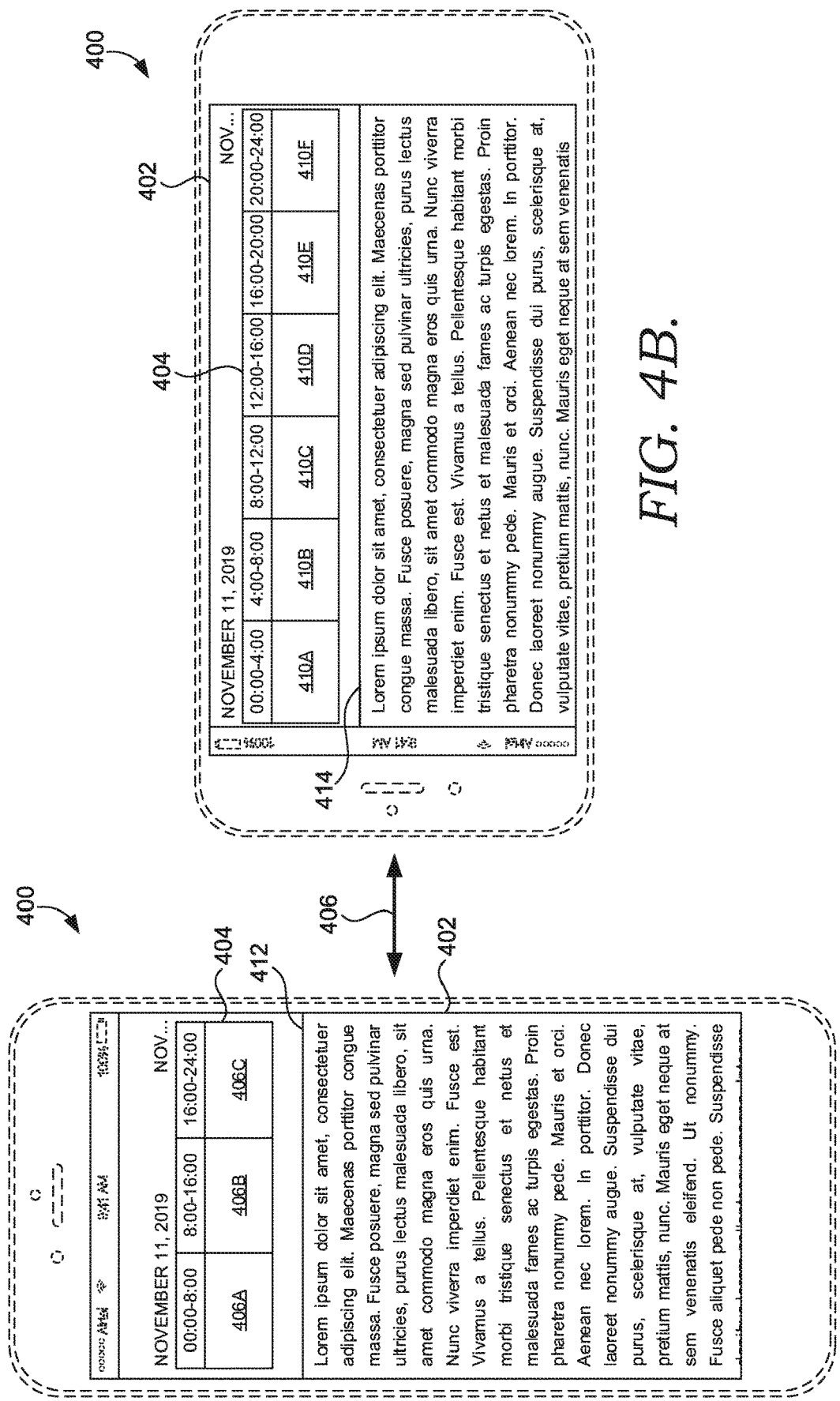
FIGS. 4A-4B illustrate a client device having a display device provided in various orientations, in accordance with an aspect described herein.

Turning now to FIGS. 4A-4B, an example client device 400 having display device 402 is provided. In FIG. 4A, client device 400 is provided in a first orientation, while in FIG. 4B, client device 400 is provided in a second orientation.

In FIG. 4A, display device 402 is illustrated as displaying a graphical user interface with example timeline 404. Timeline 404 is a columnized timeline and has been segmented into three columns 406A-406C. Each of columns 406A-406C is a one-third fractional portion of the 24-hour length of time representation. In this figure, client device 400 is represented in a first orientation that is a portrait-type orientation, where its width is less than its height. FIG. 4B illustrates client device 400 in a second orientation that is a landscape-type orientation, where its width is greater than its height.

Container 412 illustrated in FIG. 4A has a smaller width than container 414 illustrated in FIG. 4B. Thus, when rotating client device 400 from the first position to the second position, the updated container size supports a greater number of columns when segmenting timeline 404. Here, the same timeline 404 is provided, but it has been segmented into a greater number of columns, columns 410A-410F, based on the updated container size and the length of time representation. As indicated by double arrow 406, a user may rotate client device 400 in either direction. However, using the technology provided herein, the timeline would be updated to display timeline 404 in a manner that maintains context, while providing an intuitive division of the timeline. This may similarly apply where the user changes between a first client device having a first display device and a second client device having a second display device that is larger than the first display device.

In an aspect, timeline columnizer 118 can apply breakpoints to a timeline or other features associated with the timeline. Breakpoints can also be applied to a columnized timeline. In general, breakpoints define sections of the timeline or may define boundaries for other features associated with the timeline. A section can encompass one or more of the columns. Breakpoints can correspond to column ends. For example, column ends can be bordered to distinguish between two columns or the end of the timeline. By applying breakpoints corresponding to column ends, columns are not separated when sections of the timeline are provided in different arrangements. However, "applying breakpoints corresponding to column ends" is not meant to imply that all column ends have breakpoints, but rather, where a breakpoint is applied it corresponds to an end of one of the columns. Thus, in an example, 12 columns can be divided into three sections using breakpoints corresponding to the column ends of the four column groups. Applying breakpoints at column ends is beneficial because sections created by the breakpoints can be arranged on a graphical user interface in various manners to maintain context of the timeline information. Further, arranging sections or updating the arrangement of sections of a timeline allows for more of the timeline to be visible than it otherwise would be given space limitations of a container size. Where breakpoints are applied to features associated with the timeline, such as navigation features (e.g., zoom, panning, jump to date, etc.), the breakpoints can define boundaries or ends of the feature. In this way, features that are used in conjunction with the timeline can be arranged in various manners as the timeline expands or contracts in size. Thus, the timeline can expand and contract based on the display device size, while the associated features used in conjunction with the timeline are provided in arrangements that allow each feature to remain displayed, regardless of the timeline size.

Figure 5C:
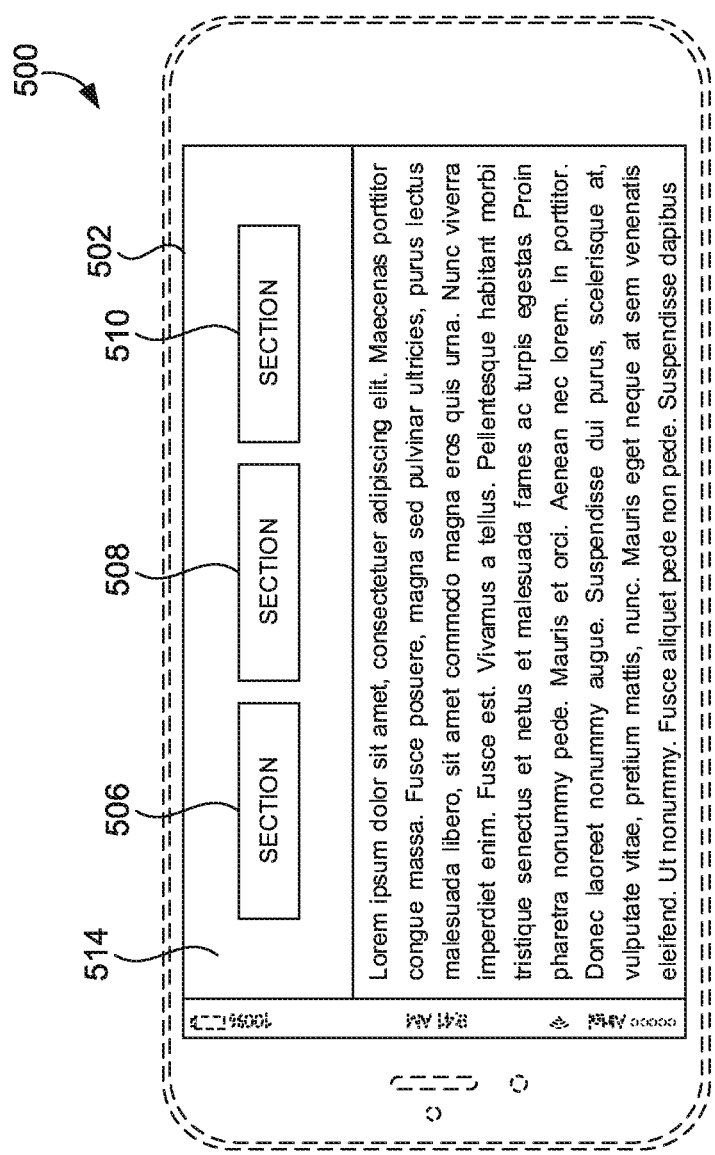

To illustrate an example, FIGS. 5A-5C are provided. FIGS. 5A-5C illustrate a client device 500 having display device 502. Beginning first with FIG. 5A, a graphical user interface is displayed on display device 502. The graphical user interface comprises container area 504 having within it first section 506, second section 508, and third section 510. Here, breakpoints have been added to each end of sections 506, 508, and 510. Together, breakpoints are intended to illustrate a single columnized timeline. Each section of sections 506, 508, and 510 is a portion of the columnized timeline. Each section could include one column or multiple columns. Breakpoints at the ends of each section are intended to correspond to column ends of columns within the sections. The columns have not been illustrated in this example for ease of describing the technology.

Based on the breakpoints, various arrangements of sections 506, 508, and 510 can be generated and provided. Sections 506, 508, and 510 can be arranged based on container size. By arranging the columnized timeline sections, some aspects allows for more of the columnized timeline to be provided based on the container size. While many different arrangements of the sections would be available, some examples are provided in FIGS. 5A-5C. The example arrangements provided herein are not intended to limit the scope of arrangements possible using the described technology.

In FIG. 5A, the graphical user interface provides container area 504 in the upper left-hand portion of display device 500. Based on a width of container area 504, the columnized timeline represented by sections 506, 508, and 510 cannot be displayed horizontally. As such, first section 506 is provided vertical and adjacent to second section 508. Similarly, second section 508 is provided vertical and adjacent to third section 510. In addition, as illustrated, second section 508 is disposed between first section 506 and third section 510.

FIG. 5B illustrates a graphical user interface providing another container area 512. Here container area 512 is provided by the graphical user interface in the upper part of display device 502. In an aspect, container area 512 may be provided in response to a change of settings by the user to manipulate display options. Here, first section 506 is shown vertical and adjacent to both second section 508 and third section 510. Further, in the arrangement provided by FIG. 5B, second section 508 is provided horizontal and adjacent to third section 510. The arrangement of sections 506, 508, and 510 illustrated in FIG. 5B may be provided in response to a change in container size. Thus, for instance, should the arrangement provided by FIG. 5A be initially provided, and the container size is updated from container area 504 to container area 512, the system can update the arrangement to that shown in FIG. 5B in response to the updated container size.

Turning now to FIG. 5C, another arrangement of sections 506, 508, and 510 is provided within container area 514.

Similarly, this arrangement may occur in response to a change in display device size that updates the container size to container area 514. For example, this could occur when changing the orientation of display device 500. In FIG. 5C, first section 506 is illustrated as horizontal and adjacent to second section 508, while second section 508 is illustrated horizontal and adjacent to third section 510. Second section 508 is further disposed between first section 506 and third section 510. In this arrangement, the columnized timeline can be viewed in a single continuous view.

Figure 6:
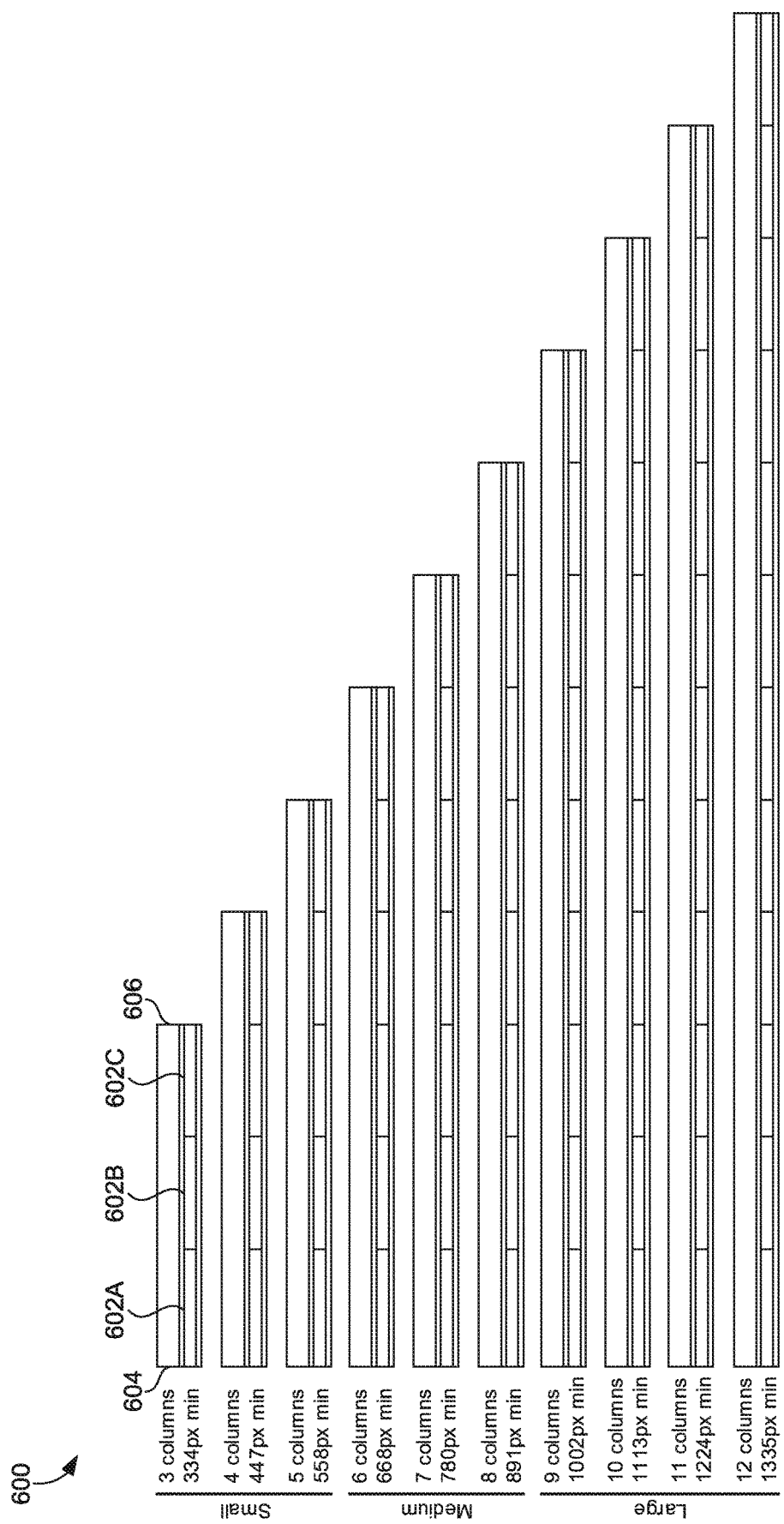
FIG. 6 is another example framework for utilization by the timeline generation system of FIG. 1, in accordance with an aspect described herein.

With reference now to FIG. 6, FIG. 6 provides an example framework 600 for applying breakpoints based on various display device sizes. In this example, the breakpoints are determined based on the number of columns and the display devices size, again with reference to "small," "medium," and "large." A container area provided by a graphical user interface displayed on the display device can be proportional to the size of the display device. The example framework provided by FIG. 6 can be used with a column width of 110 px having 1 px boarders. The breakpoints can be rounded to the highest minimum width for presentation within the container area, as previously described. For clarity, only one row in FIG. 6 has been labeled. As illustrated, framework 600 includes columns 602A-602C. Breakpoints 604 and 606 are illustrated. Breakpoint 604 corresponds to an end of column 602A, while breakpoint 606 corresponds to an end of column 602C.

Figure 7:
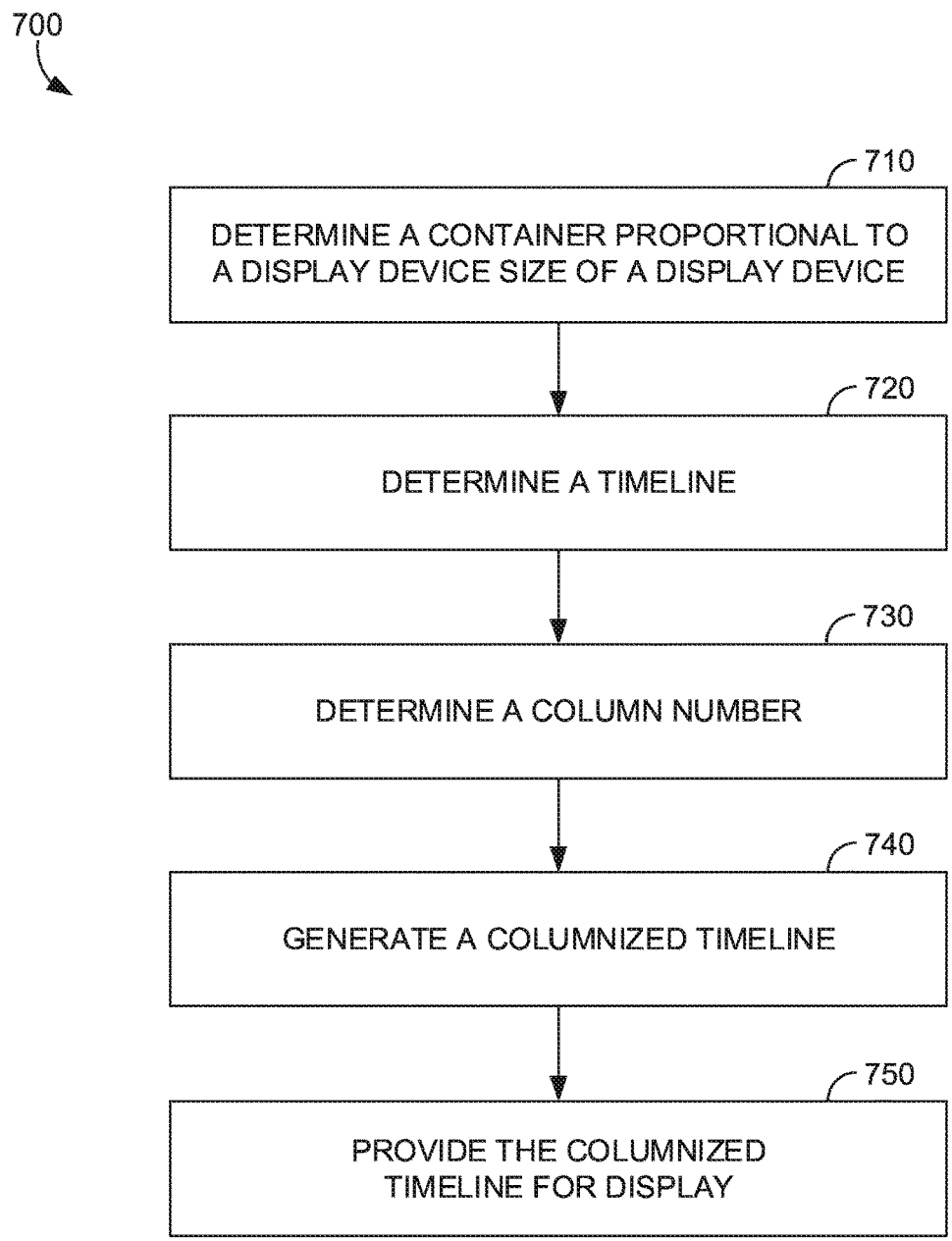
FIG. 7 is a flow diagram of an example method for providing a columnized timeline, in accordance with an aspect described herein.
Figure 8:
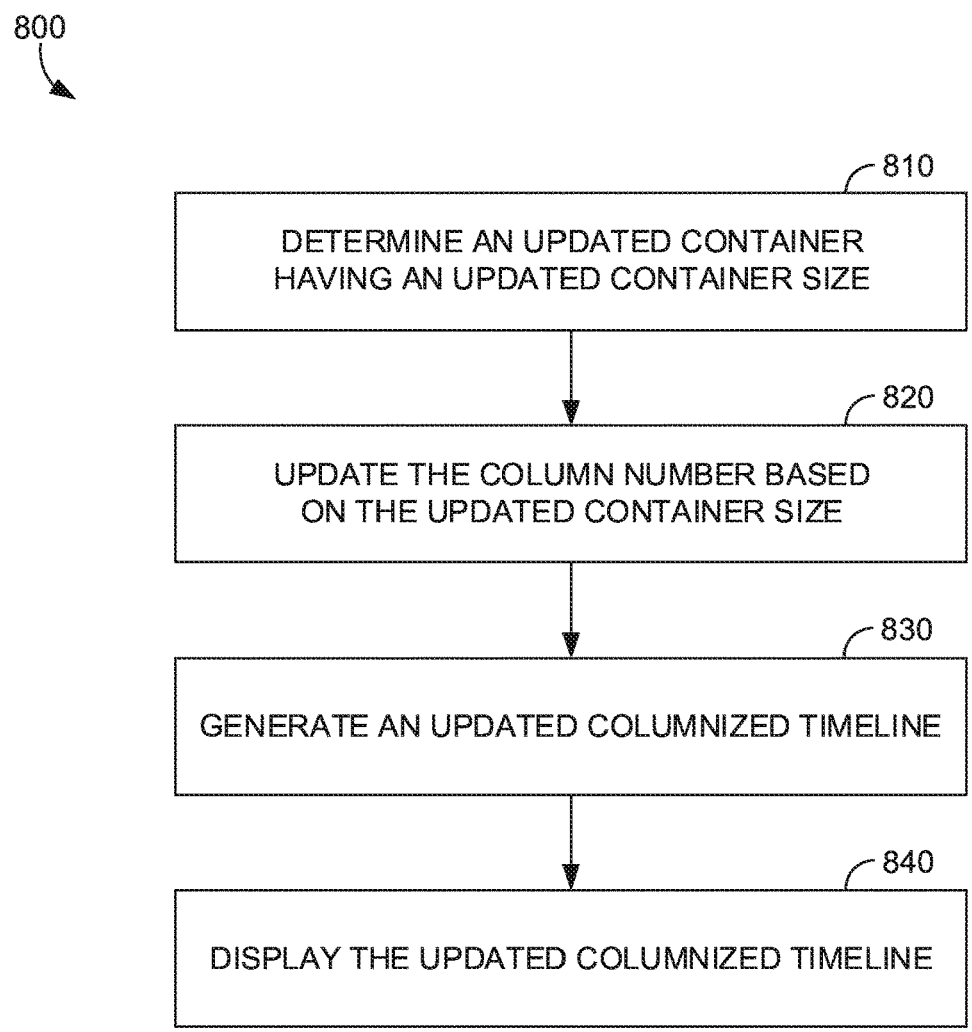
FIG. 8 is a flow diagram of an example method for generating an updated columnized timeline, in accordance with an aspect described herein.
Figure 9:
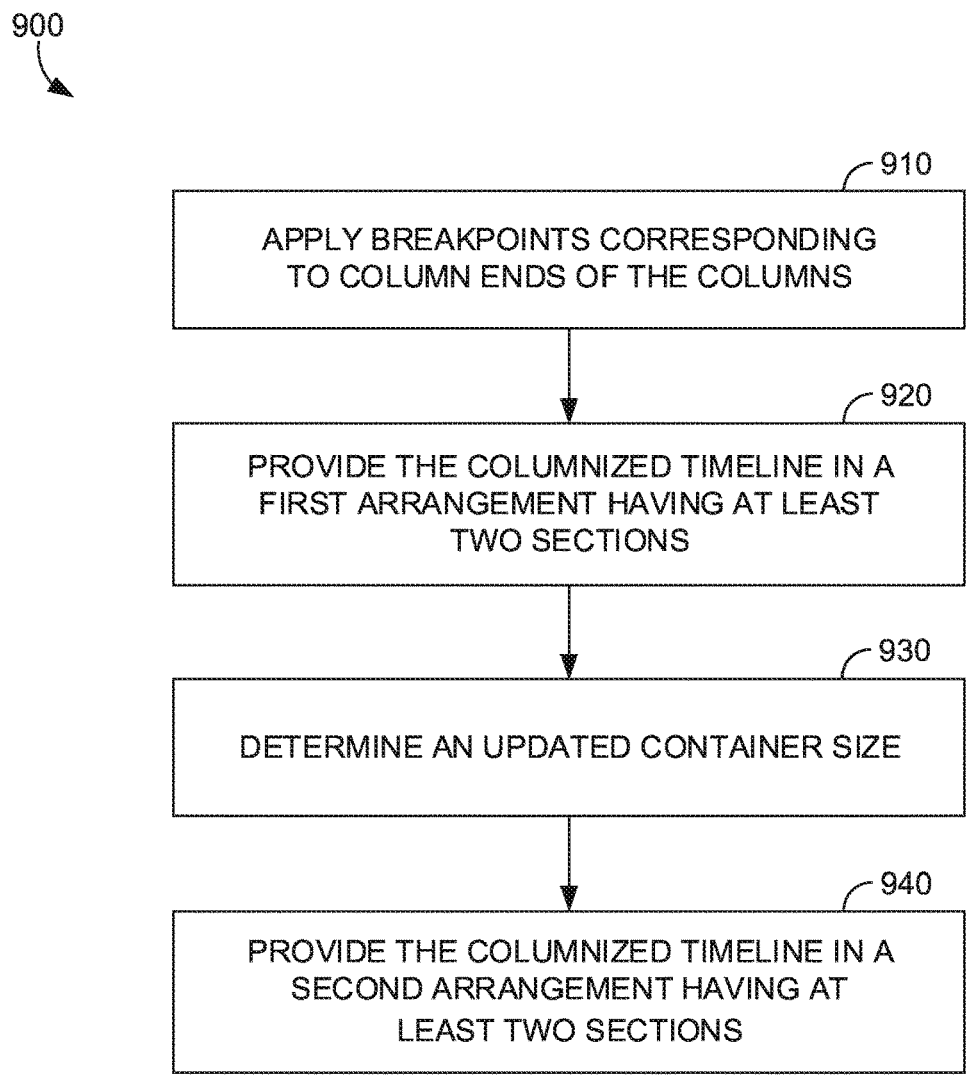
FIG. 9 is a flow diagram of an example method for providing sections of a columnized timeline, in accordance with an aspect described herein.

With reference now to FIGS. 7-9, flow diagrams are provided illustrating methods 700, 800, and 900. Each block of the methods, and any other methods described herein, can comprise a computing process performed using any combination of hardware, firmware, or software. For instance, various functions can be carried out by a processor executing instructions stored in memory. The methods can also be embodied as computer-usable instructions stored on computer storage media. The methods can be provided by a standalone application, a service or hosted service (standalone or in combination with another hosted service), or a plug-in to another product, to name a few. The methods may be implemented by timeline generation system 102 as described in conjunction with at least FIGS. 1-6.

Turning initially to FIG. 7, FIG. 7 illustrates method 700 for providing a columnized timeline at a display device. At block 710, a container proportional to the display device is determined. The container can be determined using container generator 114 of FIG. 1. The container may define a boundary of an area of a graphical user interface that is presented at the display device. At block 720, a timeline is determined. The timeline can be determined using timeline determiner 116 of FIG. 1. The timeline can be determined using received information that has a date or time associated with the information, such that the information includes a chronological order. The chronological order of information may form the timeline, which has a length of time representation based on the chronological information.

At block 730, a column number is determined. The column number can be determined using timeline columnizer 118 of FIG. 1. The column number may be based on the length of time representation and a size of the container area that is proportional to the display device. Each column may represent a range of time on the timeline, and the range of time for each column may comprise a fractional portion of the length of time representation. At block 740, a columnized timeline is generated. The columnized timeline can be generated using timeline columnizer 118 of FIG. 1. The columnized timeline can be generated by segmenting the timeline determined at block 730 into columns based on the column number. At block 750, the columnized timeline can be generated as part of the graphical user interface, which is provided via the display device.

Referencing now FIG. 8, the figure illustrates method 800 for determining and displaying an updated columnized timeline. At block 810, an updated container is determined. Based on the updated container, an updated container size may be determined. The updated container may be determined in response to a new display device that is a different size than an initial display device. In another aspect, the updated container may be determined in response to an orientation change of a display device. The updated container can be determined by container generator 114 of FIG. 1. At block 820, the column number is updated based on the updated container size. In an aspect, a same timeline may be provided for the initial container and the updated container, and thus, the container number is updated based on the updated container size. The updated column number can be determined using timeline columnizer 118.

At block 830, an updated columnized timeline is generated. The updated columnized timeline can be generated from an initial timeline corresponding to the initial columnized timeline. The initial timeline can be columnized with the updated column number by timeline columnizer 118 to generate the updated columnized timeline. At block 840, the columnized timeline can be generated as part of a graphical user interface, which is provided via the display device.

Turning now to FIG. 9, method 900 provides an example method for arranging sections of a timeline on a display device. At block 910, breakpoints are applied to a columnized timeline. The breakpoints may be applied corresponding to column ends of the columns. The breakpoints may define sections of the columnized timeline. In an aspect, there are at least two sections, a first section and a second section. The breakpoints may be applied and the sections determined using timeline columnizer 118 of FIG. 1. At block 920, the columnized timeline is presented in a first arrangement. The at least two sections may be included in the first arrangement. In an example, the first section may be provided horizontal and adjacent to the second section. The first arrangement may be associated with a first orientation of the display device.

At block 930, an updated container size is determined. The updated container size may be determined by container generator 114 of FIG. 1, and in one example, may be determined based on the display device being rotated from the first orientation to a second orientation. At block 940, the columnized timeline may be presented in a second arrangement that includes the at least two sections. The second arrangement may be provided in response to the updated container size. In an example second arrangement, the first section is horizontal and adjacent to the second section. Thus, the second arrangement may be associated with the second orientation of the display device.

Having described an overview of embodiments of the present technology, an example operating environment in which embodiments of the present technology may be implemented is described below in order to provide a general context for various aspects. Referring now to FIG. 10, in particular, an exemplary operating environment for implementing embodiments of the present invention is shown and designated generally as computing device 1000. Computing device 1000 is but one example of a suitable computing environment and is not intended to suggest any limitation as to the scope of use or functionality of the invention. Neither should computing device 1000 be interpreted as having any dependency or requirement relating to any one or combination of components illustrated.

The invention may be described in the general context of computer code or machine-useable instructions, including computer-executable instructions such as program modules, being executed by a computer or other machine, such as a cellular telephone, personal data assistant or other handheld device. Generally, program modules including routines, programs, objects, components, data structures, etc., refer to code that perform particular tasks or implement particular abstract data types. The invention may be practiced in a variety of system configurations, including hand-held devices, consumer electronics, general-purpose computers, more specialty computing devices, etc. The invention may also be practiced in distributed computing environments where tasks are performed by remote-processing devices that are linked through a communications network.

With reference to FIG. 10, computing device 1000 includes bus 1010 that directly or indirectly couples the following devices: memory 1012, one or more processors 1014, one or more presentation components 1016, input/output (I/O) ports 1018, input/output components 1020, and illustrative power supply 1022. Bus 1010 represents what may be one or more busses (such as an address bus, data bus, or combination thereof). Although the various blocks of FIG. 10 are shown with lines for the sake of clarity, in reality, delineating various components is not so clear, and metaphorically, the lines would more accurately be grey and fuzzy. For example, one may consider a presentation component such as a display device to be an I/O component. Also, processors have memory. The inventor recognizes that such is the nature of the art, and reiterates that the diagram of FIG. 10 is merely illustrative of an exemplary computing device that can be used in connection with one or more embodiments of the present invention. Distinction is not made between such categories as "workstation," "server," "laptop," "hand-held device," etc., as all are contemplated within the scope of FIG. 10 and reference to "computing device."

Computing device 1000 typically includes a variety of computer-readable media. Computer-readable media can be any available media that can be accessed by computing device 1000 and includes both volatile and nonvolatile media, and removable and non-removable media. By way of example, and not limitation, computer-readable media may comprise computer storage media and communication media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by computing device 1000. Computer storage media does not comprise signals per se. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

Memory 1012 includes computer-storage media in the form of volatile or nonvolatile memory. The memory may be removable, non-removable, or a combination thereof. Exemplary hardware devices include solid-state memory, hard drives, optical-disc drives, etc. Computing device 1000 includes one or more processors that read data from various entities such as memory 1012 or I/O components 1020. Presentation component(s) 1016 present data indications to a user or other device. Exemplary presentation components include a display device, speaker, printing component, vibrating component, etc.

I/O ports 1018 allow computing device 1000 to be logically coupled to other devices including I/O components 1020, some of which may be built in. Illustrative components include a microphone, joystick, game pad, satellite dish, scanner, printer, wireless device, etc. The I/O components 1020 may provide a natural user interface (NUI) that processes air gestures, voice, or other physiological inputs generated by a user. In some instances, inputs may be transmitted to an appropriate network element for further processing. An NUI may implement any combination of speech recognition, stylus recognition, facial recognition, biometric recognition, gesture recognition both on screen and adjacent to the screen, air gestures, head and eye tracking, and touch recognition (as described in more detail below) associated with a display of computing device 1000. Computing device 1000 may be equipped with depth cameras, such as stereoscopic camera systems, infrared camera systems, RGB camera systems, touchscreen technology, and combinations of these, for gesture detection and recognition. Additionally, the computing device 1000 may be equipped with accelerometers or gyroscopes that enable detection of motion. The output of the accelerometers or gyroscopes may be provided to the display of computing device 1000 to render immersive augmented reality or virtual reality.

Embodiments described herein support timeline generation that maintains context and provides information in an intuitive manner. The components described herein refer to integrated components of the timeline generation system. The integrated components refer to the hardware architecture and software framework that support functionality using the product determination system. The hardware architecture refers to physical components and interrelationships thereof and the software framework refers to software providing functionality that can be implemented with hardware embodied on a device.

The end-to-end software-based timeline generation system can operate within the timeline generation components to operate computer hardware to generate intuitive timelines that maintain context. At a low level, hardware processors execute instructions selected from a machine language (also referred to as machine code or native) instruction set for a given processor. The processor recognizes the native instructions and performs corresponding low-level functions relating, for example, to logic, control and memory operations. Low-level software written in machine code can provide more complex functionality to higher levels of software. As used herein, computer-executable instructions includes any software, including low level software written in machine code, higher level software such as application software and any combination thereof. In this regard, the timeline generation system components can manage resources and provide services for the system's functionality. Any other variations and combinations thereof are contemplated with embodiments of the present invention.

Having identified various components in the present disclosure, it should be understood that any number of components and arrangements may be employed to achieve the desired functionality within the scope of the present disclosure. For example, the components in the embodiments depicted in the figures are shown with lines for the sake of conceptual clarity. Other arrangements of these and other components may also be implemented. For example, although some components are depicted as single components, many of the elements described herein may be implemented as discrete or distributed components or in conjunction with other components, and in any suitable combination and location. Some elements may be omitted altogether. Moreover, various functions described herein as being performed by one or more entities may be carried out by hardware, firmware, and/or software, as described below. For instance, various functions may be carried out by a processor executing instructions stored in memory. As such, other arrangements and elements (e.g., machines, interfaces, functions, orders, and groupings of functions, etc.) can be used in addition to or instead of those shown.

Embodiments described above may be combined with one or more of the specifically described alternatives. In particular, an embodiment that is claimed may contain a reference, in the alternative, to more than one other embodiment. The embodiment that is claimed may specify a further limitation of the subject matter claimed.

The subject matter of the present technology is described with specificity herein to meet statutory requirements. However, the description itself is not intended to limit the scope of this disclosure. Rather, the inventors have contemplated that the claimed or disclosed subject matter might also be embodied in other ways, to include different steps or combinations of steps similar to the ones described in this document, in conjunction with other present or future technologies. Moreover, although the terms "step" or "block" might be used herein to connote different elements of methods employed, the terms should not be interpreted as implying any particular order among or between various steps herein disclosed unless and except when the order of individual steps is explicitly stated.

Within this disclosure, "communicating" and "in communication" have the same broad meaning as the word "receiving," or "transmitting" facilitated by software or hardware-based buses, receivers, or transmitters" using communication media described herein. Also, the word "initiating" has the same broad meaning as the word "executing or "instructing" where the corresponding action can be performed to completion or interrupted based on an occurrence of another action. In addition, words such as "a" and "an," unless otherwise indicated to the contrary, include the plural as well as the singular. Thus, for example, the constraint of "a feature" is satisfied where one or more features are present. Also, the term "or" includes the conjunctive, the disjunctive, and both (a or b thus includes either a or b, as well as a and b).

For purposes of a detailed discussion above, embodiments of the present technology described with reference to a distributed computing environment; however the distributed computing environment depicted herein is merely an example. Components can be configured for performing novel aspects of embodiments, where the term "configured for" can refer to "programmed to" perform particular tasks or implement particular abstract data types using code.

Further, while embodiments of the present technology may generally refer to the timeline generation system, it is understood that the techniques described may be extended to other implementation contexts.

From the foregoing, it will be seen that this technology is one well adapted to attain all the ends and objects described above, including other advantages that are obvious or inherent to the structure. It will be understood that certain features and subcombinations are of utility and may be employed without reference to other features and subcombinations. This is contemplated by and is within the scope of the claims. Since many possible embodiments of the described technology may be made without departing from the scope, it is to be understood that all matter described herein or illustrated the accompanying drawings is to be interpreted as illustrative and not in a limiting sense.

What is claimed is:

1. One or more computer storage media having computer-useable instructions that, when used by one or more computing devices, cause the one or more computing devices to perform operations for providing a timeline for display at a display device, the operations comprising:
    determining a container proportional to a display device size, the container defining a boundary of an area for display;
    determining a timeline, the timeline having a length of time representation;
    determining a column number by:
        identifying a plurality of column numbers for a length of time representation based on divisibility of the length of time representation for each column number; and
        selecting the column number from the plurality of column numbers having been identified based on a largest column number supported by the container, each column of the column number representing a range of time on the timeline, the range of time for each column comprising an equal fractional portion of the length of time representation;
    generating a columnized timeline by segmenting the timeline into columns based on the column number;
    providing the columnized timeline for display;
    determining an updated container having an updated container size proportional to a change in the display device size;
    updating the column number based on the updated container size;
    generating an updated columnized timeline by segmenting the timeline into the columns based on the updated column number; and
    providing the updated columnized timeline for display.

2. The computer storage media of claim 1, further comprising:
    applying breakpoints corresponding to column ends of the columns; and
    providing the columnized timeline in at least two sections, the at least two sections defined by the breakpoints.

3. The computer storage media of claim 2, wherein a first section of the at least two sections is provided horizontal and adjacent to a second section of the at least two sections.

4. The computer storage media of claim 2, wherein a first section of the at least two sections is provided vertical and adjacent to a second section of the at least two sections.

5. The computer storage media of claim 3, further comprising:
    providing a first section of the at least two sections horizontal and adjacent to a second section of the at least two sections; and
    based on the updated container size, providing the first section vertical and adjacent to the second section.

6. The computer storage media of claim 1, wherein the container size and the columns are based on a number of pixels.

7. A computerized method for providing a timeline display, the method comprising:
    determining a column number based on a container size of a container that defines a boundary of an area within a display device, each column representing an equal fractional portion of a length of time representation of a timeline, wherein the column number is determined by:
        identifying a plurality of column numbers for a length of time representation based on divisibility of the length of time representation for each column number; and
        selecting the column number from the plurality of column numbers having been identified based on a largest column number supported by the container;
    generating a columnized timeline by segmenting the timeline into columns based on the column number;
    providing the columnized timeline for display at the display device, wherein the columnized timeline is provided within the container;
    generating an updated columnized timeline based on an updated container size proportional to a change in a display device size; and
    providing the updated columnized timeline for display at the display device.

8. The method of claim 7, further comprising
    applying breakpoints corresponding to column ends of the columns; and
    providing the columnized timeline in at least two sections, the at least two sections defined by the breakpoints.

9. The method of claim 8, wherein a first section of the at least two sections is provided horizontal and adjacent to a second section of the at least two sections.

10. The method of claim 8, wherein a first section of the at least two sections is provided vertical and adjacent to a second section of the at least two sections.

11. The method of claim 8, further comprising:
    providing a first section of the at least two sections horizontal and adjacent to a second section of the at least two sections; and
    based on the updated container size, providing the first section vertical and adjacent to the second section.

12. The method of claim 7, wherein the container size and the columns are based on a number of pixels.

13. A computer system comprising:
    a display device;
    at least one processor;
    computer storage media having instructions stored thereon that when executed by the at least one processor, cause the at least one processor to:
        determine a container proportional to a display device size of a display device, the container defining a boundary of an area within the display device;
        for a timeline comprising a length of time representation, determine a column number based on a container size of the container and the length of time representation of the timeline, each column representing a range of time on the timeline, the range of time for each column comprising an equal fractional portion of the length of time representation, wherein the column number is determined by
identifying a plurality of column numbers for a length of time representation based on divisibility of the length of time representation for each column number; and
selecting the column number from the plurality of column numbers having been identified based on a largest column number supported by the container;
generate a columnized timeline by segmenting the timeline into columns based on the column number;
display the columnized timeline at the display device;
determine an updated container having an updated container size proportional to a change in the display device size;
update the column number based on the updated container size;
generate an updated columnized timeline by segmenting the timeline into the columns based on the updated column number; and
display the updated columnized timeline at the display device.

14. The system of claim 13, further comprising:
apply breakpoints corresponding to column ends of the columns; and
provide the columnized timeline in at least two sections, the at least two sections defined by the breakpoints, wherein a first section of the at least two sections is provided horizontal and adjacent to a second section of the at least two sections.

15. The system of claim 14, further comprising:
based on the updated container size, provide the first section vertical and adjacent to the second section.

16. The system of claim 13, wherein the updated container size is determined in response to the display device rotating from a landscape orientation to a portrait orientation.

17. The system of claim 13, further comprising:
apply breakpoints corresponding to column ends of the columns; and
provide the columnized timeline in at least two sections, the at least two sections defined by the breakpoints, wherein a first section of the at least two sections is provided vertical and adjacent to a second section of the at least two sections.

* * * * *